United States Patent [19]

Teutsch et al.

[11] 4,168,306

[45] Sep. 18, 1979

[54] 17α-ACETYLENIC-Δ⁴-ANDROSTENES

[75] Inventors: Jean G. Teutsch, Le Blanc-Mesnil; Roger Deraedt, Pavillons-sous-Bois, both of France

[73] Assignee: Roussel Uclaf, Paris, France

[21] Appl. No.: 878,907

[22] Filed: Feb. 17, 1978

[30] Foreign Application Priority Data

Feb. 22, 1977 [FR] France ........................... 77 05066
Jan. 9, 1978 [FR] France ........................... 78 00405

[51] Int. Cl.² .................................................. A61K 31/56
[52] U.S. Cl. ............................... 424/243; 260/397.45; 260/239.55 C
[58] Field of Search ..................................
/Machine Searched Steroids

[56] References Cited

U.S. PATENT DOCUMENTS

| | | | |
|---|---|---|---|
| 2,702,811 | 2/1955 | Colton | 260/397.45 |
| 2,740,798 | 4/1956 | Ralls | 260/397.45 |
| 3,127,314 | 3/1964 | Goffinet et al. | 424/243 |
| 3,308,025 | 3/1967 | Destuches | 424/243 |
| 3,442,918 | 5/1969 | Feather et al. | 260/397.4 |

Primary Examiner—Ethel G. Love
Attorney, Agent, or Firm—Hammond & Littell

[57] ABSTRACT

17α-Acetylenic-Δ⁴-androstenes of the formula

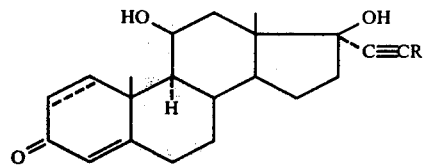

wherein R is saturated or unsaturated alkyl of 1 to 12 carbon atoms and the dotted line indicates the optional presence of a double bond in the 1(2) position of the A ring with the proviso that R is not methyl when the A ring has only one double bond having a remarkable local anti-inflammatory activity and a process for their preparation.

23 Claims, No Drawings

17α-ACETYLENIC-Δ⁴-ANDROSTENES

STATE OF THE ART

U.S. Pat. Nos. 2,740,798 and 3,308,025 describe 11β-hydroxy-17α-ethynyl-steroids which are not substituted in the 17α-position as the compounds of formula I. U.S. Pat. No. 3,793,308 names 21-methyl-Δ⁴-pregnene-11β,17β-diol-20-yne-3-one but there is no description of how to prepare the compound. U.S. Pat. Nos. 3,127,428 and 3,221,033 have extremely large generic formulas which encompass the compounds of formula I but do not suggest the compounds of formula I nor a process for their preparation.

OBJECTS OF THE INVENTION

It is an object of the invention to provide the novel 17α-acetylenic-Δ⁴-androstenes of formula I and a novel process for their preparation.

It is another object of the invention to provide novel topical anti-inflammatory compositions without secondary cortisonic side effects and to a novel method of relieving inflammation in warm-blooded animals.

These and other objects and advantages of the invention will become obvious from the following detailed description.

THE INVENTION

The novel 17α-acetylenic-Δ⁴-androstenes of the invention have the formula

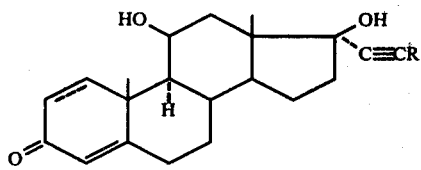

wherein R is saturated or unsaturated alkyl of 1 to 12 carbon atoms and the dotted line indicates the optional presence of a double bond in the 1(2) position of the A ring with the proviso that R is not methyl when the A ring has only one double bond.

Examples of alkyl groups for R are saturated alkyl such as methyl, ethyl, propyl, isopropyl, n-butyl, isobutyl, n-pentyl, n-hexyl, 2-methyl-pentyl, 2,3-dimethyl-butyl, n-octyl and 2,2-dimethylhexyl and unsaturated alkyl such as vinyl, isopropenyl, isobutenyl, allyl and 2-methyl-allyl.

Among the preferred compounds of the invention are those wherein the A ring has only one double bond in the 4(5) position and R is other than methyl and those wherein the A ring has double bonds in the 1(2) and 4(5) positions. Specific novel compounds of the invention are 21-ethyl-Δ⁴-pregnene-11β,17β-diol-20-yne-3-one, 21-methyl-Δ¹,⁴-pregnadiene 11β,17β-diol-20-yne-3-one, 21-ethyl-Δ¹,⁴-pregnadiene-11β,17β-diol-20-yne-3-one and 21-isopropenyl-Δ¹,⁴-pregnadiene-11β,17β-diol-20-yne-3-one.

The novel local anti-inflammatory compositions are comprised of an anti-inflammatorily effective amount of at least one compound of the formula

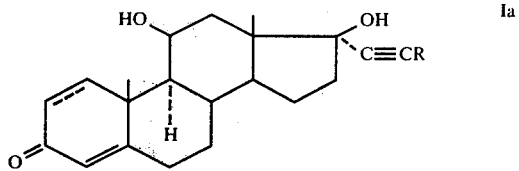

wherein R is saturated and unsaturated alkyl of 1 to 12 carbon atoms and the dotted line indicates the optional presence of a 1(2) double bond in the A ring and an inert pharmaceutical carrier. The compositions may be in the form of powders, pomades, creams, gels and aerosol preparations as well as tablets, coated tablets, cachets, capsules, granules, emulsions, syrups, suppositories and injectable solutions or suspensions.

Examples of suitable excipients or carriers are talc, starch, aqueous or non-aqueous vehicles, fatty bodies of animals or vegetable origin, paraffinic derivatives, glycols, diverse wetting agents, dispersants or emulsifiers and preservatives.

The compositions of the invention have the advantage of having a dissociation between anti-inflammatory properties when applied locally or generally and therefore may be used locally without the classic cortisonic sideeffects. Therefore, they are useful for treatment of local inflammatory reactions such as edemas, dermatosis, pruritsis, diverse forms of eczema and solair erythema. They are equally useful for the treatment of polyarthritis, arthrosis and lombalgia.

Among the preferred compositions of the invention are those wherein the compound of formula Ia is 21-methyl-Δ⁴-pregnene-11β,17β-diol-20-yne-3-one, 21-ethyl-Δ⁴-pregnene-11β,17β-diol-20 -yne-3-one, 21-ethyl-Δ¹,⁴-pregnadiene-11β,17β-diol-20-yne-3-one, 21-isopropenyl-Δ¹,⁴-pregnadiene-11β,17β-diol-20-yne-3-one and especially 21-methyl-Δ¹,⁴-pregnadiene-11β,17β-diol-20-yne-3-one.

The novel method of the invention of relieving local inflammation in warm-blooded animals, including humans, comprises administering to warm-blooded animals an anti-inflammatorily effective amount of at least one compound of formula Ia. The compounds are preferably administered topically and may be 0.1 to 5% of the composition with the compound of the example 3. When administered orally, the dose may be administered at 0,2 to 20 mg/kg with the compound of the example 3.

The novel process of the invention for the preparation of a compound of formula Ia comprises reacting a compound of the formula

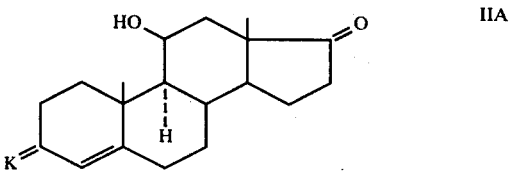

wherein K is a blocked keto group in the form of an oxime or ketal or a compound of the formula

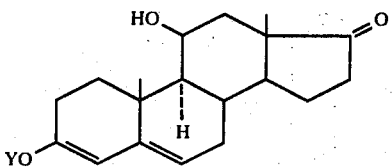 IIB wherein Y is alkyl of 1 to 4 carbon atoms with an alkynyl magnesium halide of the formula

wherein R has the above definition and Hal is a halogen and reacting the latter with an acid hydrolysis agent to obtain a compound of the formula

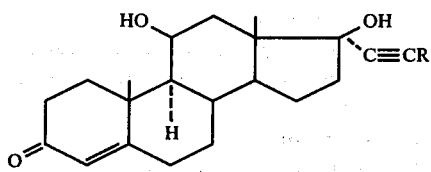 I' which, if desired, may be reacted with the deshydrogenation agent to obtain a compound of the formula

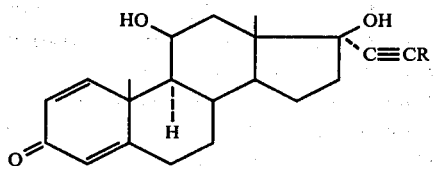 I''

When K is a ketal group, it is preferably a cycloalkyl ketal of 2 to 4 carbon atoms such as ethyleneketal or propyleneketal or a dialkylketal of 1 to 4 alkyl carbon atoms such as dimethylketal or diethylketal. When K is a blocked keto group in the form of an oxime, it is preferably a NOH or NOAlK group where AlK is 1 to 4 carbon atoms.

Y is preferably methyl, ethyl or n-propyl and Hal is preferably bromine. The preferred acid hydrolysis agents are hydrochloric acid, sulfuric acid, acetic acid, citric acid, or p-toluene sulfonic acid. The deshydrogenation is preferably effected biochemically, preferably with Arthrobacter Simplex UC 1047 but equally useful are chemical means such as with chloranil or other p-benzoquinone derivatives such as 2,3-dichloro-5,6-dicyano-benzoquinone.

In a preferred mode of the process to prepare 21-methyl-$\Delta^4$pregnene-11$\beta$,17$\beta$-diol-20-yne-3-one comprises reacting a compound of formula II$_A$ or II$_B$ with a propynyl magnesium halide and the resulting product is reacted with an acid hydrolysis agent. The compound of formula II$_B$ is preferably 3-ethoxy-$\Delta^{3,5}$-androstadiene-11$\beta$-ol17-one and the acid hydrolysis agent is hydrochloric acid.

In a variation of the process of the invention to produce a compound of formula I$_a$, a compound of the formula

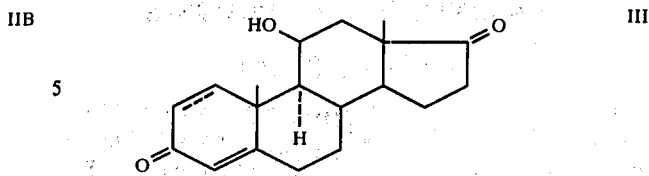 III is reacted with a compound of the formula H—C≡CR in the presence tertiary alcoholate to produce the corresponding compound of formula Ia. Preferably, the tertiary alcoholate is an alkali metal tertiary alcoholate such as sodium, potassium or lithium tertiary amylate or tert.-butylate. This process is preferred for the compounds of formula Ia wherein there is only the 4(5) double bond in the A ring.

The compounds of formula III are known and may be prepared by the process described in U.S. Pat. Nos. 3,072,684 and 3,010,957. The compounds of formulae II$_A$ and II$_B$ are also known and may be prepared as described in U.S. Pat. No. 3,072,684.

In the following examples there are described several preferred embodiments to illustrate the invention. However, it is to be understood that the invention is not intended to be limited to the specific embodiments.

EXAMPLE 1

21-methyl-$\Delta^4$-pregnene-11$\beta$,17$\beta$-diol-20-yne-3-one

STEP A: 3-ethoxy-$\Delta^{3,5}$-androstadiene-11$\beta$-ol-17-one

A mixture of 43 g of $\Delta^4$-androstene-11$\beta$-ol-3,17-dione (prepared as in U.S. Pat. No. 3,072,684), 215 ml of ethanol and 43 ml of a 0.26 M ethyl orthoformate solution was heated to 50° C. and 5.2 ml of a solution of 0.48 g of p-toluene sulfonic acid in 50 ml of ethanol were added thereto. The solution was held at 50° C. for 5 minutes and after the addition of 8.6 ml of triethylamine thereto, the mixture was cooled to 20° C. 258 ml of water were added to the mixture which was then stirred for one hour at 0° to 5° C. The mixture was filtered and the recovered product was washed with a 50–50–0.5 mixture of ethanol-water-pyridine to obtain 40.1 g of 3-ethoxy-$\Delta^{3,5}$-androstadiene-11$\beta$-ol-17-one which is used as is for the next step.

STEP B:

21-methyl-$\Delta^4$-pregnene-11$\beta$,17$\beta$-diol-20-yne-3-one

Propyne was bubbled through 70 ml of a solution of 0.75 M of ethyl magnesium bromide in tetrahydrofuran cooled to 0° C. for 2 hours and then the temperature of the mixture was allowed to return to room temperature. 3.45 g of the product of Step A and 14 ml of dry tetrahydrofuran were added thereto and the mixture was held at 20°–25° C. for 45 minutes and was then poured into a 2 N hydrochloric acid solution. The mixture was extracted with ether and the ether phase was washed with water and purified to obtain 21-methyl-$\Delta^4$-pregnene-11$\beta$,17$\beta$-diol-20-yne-3-one melting at 223° C.

EXAMPLE 2

21-ethyl-$\Delta^4$-pregnene-11$\beta$,17$\beta$-diol-20-yne-3-one

Butyne was bubbled for 40 minutes through 65 ml of a solution of 0.82 M of ethyl magnesium bromide in tetrahydrofuran cooled to 0° C. and the temperature was then allowed to return to room temperature. 3 g of 3-ethoxy-$\Delta^{3,5}$-androstadiene-11$\beta$,17$\beta$-diol-20-yne-3-one were added thereto and the mixture was stirred for one hour and was then poured in aqueous ammonium chloride solution. The mixture was extracted with ether and the ether phase was dried over sodium sulfate and evaporated to dryness under reduced pressure. The residue was chromatographed over silica gel and was eluted with a 8-2 benzene-ethyl acetate mixture containing 0.2% triethylamine. The 2.1 g of product was taken up in 25 ml of N hydrochloric acid and 125 ml of methanol and the solution was poured into a saturated sodium chloride solution. The mixture was extracted with methylene chloride and the organic phase was dried over sodium sulfate and evaporated to dryness to obtain 1.62 g of raw product. The latter was chromatographed over silica gel and was eluted with a 1—1 benzene-ethyl acetate mixture to obtain 1.37 g of 21-ethyl-$\Delta^4$-pregnene-11$\beta$,17$\beta$-diol-20-yne-3-one melting at 170° C. and having a specific rotation of $[\alpha]_D^{20} = 49.5° \pm 2.5°$ (c=0.5% in chloroform).

EXAMPLE 3

21-methyl-$\Delta^{1,4}$-pregnadiene-11$\beta$,17$\beta$-diol-20-yne-3-one

Propyne was bubbled through a solution of 3.1 g of potassium tert.-butylate in 50 ml of dioxane and a mixture of 2 g of $\Delta^{1,4}$-androstadiene-11$\beta$-ol-3,17-dione (prepared as in U.S. Pat. No. 2,902,498) and 25 ml of dioxane were added thereto. The mixture was stirred for 5 hours at room temperature and was then poured into 50 ml of a 1-3 acetic acid-water mixture with stirring. The mixture was diluted with 500 ml of water and was extracted with chloroform. The organic phase was washed with sodium bicarbonate solution, then with water, dried and evaporated to dryness to obtain 2.2 g of raw product. The latter was chromatographed over silica gel and was eluted with an 8-2 chloroform-acetone mixture to obtain 760 mg of a product with an Rf=0.24. The latter was crystallized from isopropyl ether to obtain 391 mg of 21-methyl-$\Delta^{1,4}$-pregnadiene-11$\beta$,17$\beta$-diol-20-yne-3-one melting at 230° C. and having a specific rotation of $[\alpha]_D^{20} = -6.5° \pm 2°$ (c=0.6% in chloroform).

EXAMPLE 4

21-ethyl-$\Delta^{1,4}$-pregnadiene-11$\beta$,17$\beta$-diol-20-yne-3-one

Using the procedure of Example 3, 1-butyne and $\Delta^{1,4}$-androstadiene-11$\beta$-ol-3,17-dione were reacted to obtain 21-ethyl-$\Delta^{1,4}$-pregnadiene-11$\beta$,17$\beta$-diol-20-yne-3-one melting at 192° C. and having a specific rotation of $[\alpha]_D^{20} = -6.5° \pm 1.5°$ (c=0.6% in CHCl$_3$).

EXAMPLE 5

21-isopropenyl-$\Delta^{1,4}$-pregnadiene-11$\beta$,17$\beta$-diol-20-yne-3-one

Using the procedure of Example 2, isopropenyl acetylene and $\Delta^{1,4}$-androstadiene-11$\beta$-ol-3,17-dione were reacted to obtain 21-isopropenyl-$\Delta^{1,4}$-pregnadiene-11$\beta$,17$\beta$-diol-20-yne-3-one melting at 218° C. and having a specific rotation of $[\alpha]_D^{20} = -20° \pm 1.5°$ (c=0.8% in CHCl$_3$).

EXAMPLE 6

Pomades were prepared containing 1.5 g of the product of Example 1 or 0.5 g of the product of Example 3 with sufficient excipient of lanoline and vaseline to obtain a final weight of 100 g. Tablets were prepared containing 5 mg of the product of Example 3 and sufficient excipient of talc, starch and magnesium stearate to obtain a final weight of 350 mg.

PHARMACOLOGICAL DATA 21-methyl-$\Delta^4$-pregnene-11$\beta$,17$\beta$-diol-20-yne-3-one (product A), 21-ethyl-$\Delta^4$-pregnene-11$\beta$,17$\beta$-diol-20-yne-3-one (product B) and 21-methyl-$\Delta^{1,4}$-pregnadiene-11$\beta$,17$\beta$-diol-20-yne-3-one (product C) were compared with hydrocortisone in an aqueous dispersion of 0.25% of carboxymethyl cellulose and 0.20% of polysorbate 80.

A. Oral anti-inflammatory activity

The anti-inflammatory activity was determined by the granuloma test of Meier et al [Experientia, Vol. 6 (1950) p. 469], slightly modified. Female Wistar rats weighing 100 to 110 g received an implantation of 2 cotton pellets weighing 10 mg each under the thorax skin. The oral treatment began after the implantation for 2 days with 2 administrations per day. 16 hours after the last ingestion or on the third day, the animals were killed and the pellets along with the granuloma tissue formed were weighed in the fresh state and after drying at 60° C. for 18 hours, the granuloma weight was determined by substracting the initial cotton weight and the DA$_{50}$ (dose which inhibited granuloma by 50%) are reported in Table I.

B. Dermic activity

The croton edema test of Tonelli et al [Endocrinology, Vol. 77 (1965), p. 625] was used in which edema was provoked in mice by application of croton oil on the ear. One group of mice had croton oil solution applied to the right ear and the second group of mice had a croton oil solution containing the test product or hydrocortisone applied to the right ear. After 6 hours, the ears were cut off and weighed with the weight difference of the left and right ears determining the degree of inflammation to determine the CA$_{50}$ dose (active concentration which diminished the edema caused by croton oil by 50%) is reported in Table I.

TABLE I

| Product | Test A mg/kg | Test B mg/ml |
|---|---|---|
| A | 50 | 0.6 |
| B | 50 | 0.6 |
| C | 8 | 0.08 |
| hydrocortisone | 15 | 2.5 |

Products A and B are much more active than hydrocortisone in the inhibition of granuloma while products A, B and C are more active locally than hydrocortisone.

Various modifications of the products and methods of the invention may be made without departing from the spirit or scope thereof and it should be understood that the invention is intended to be limited only as defined in the appended claims.

We claim:

1. 17$\alpha$-acetylene-$\Delta^4$-androstene of the formula

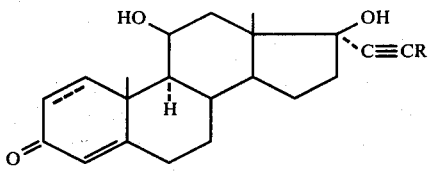

wherein R is saturated or unsaturated alkyl of 1 to 12 carbon atoms and the dotted line indicates the optional presence of a double bond in the 1(2) position of the A ring with the proviso that R is not methyl when the A ring has only one double bond.

2. A compound of claim 1 wherein the compound contains a double bond only in the 4(5) position.

3. A compound of claim 1 wherein the compound contains a double bond in both the 1(2) and 4(5) positions.

4. A compound of claim 1 wherein the compound is 21-ethyl-$\Delta^4$-pregnene-11$\beta$,17$\beta$-diol-20-yne-3-one.

5. A compound of claim 1 wherein the compound is 21-ethyl-$\Delta^{1,4}$-pregnadiene-11$\beta$,17$\beta$-diol-20-yne-3-one.

6. A compound of claim 1 wherein the compound is 21-isopropenyl-$\Delta^{1,4}$-pregnadiene-11$\beta$,17$\beta$-diol-20-yne-3-one.

7. A compound of claim 1 wherein the compound is 21-methyl-$\Delta^{1,4}$-pregnadiene-11$\beta$,17$\beta$-diol-20-yne-3-one.

8. An anti-inflammatory composition comprising an anti-inflammatory effective amount of at least one compound of the formula

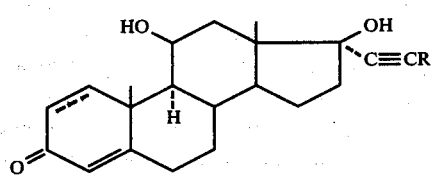

wherein R is saturated and unsaturated alkyl of 1 to 12 carbon atoms and the dotted line indicates the optional presence of a 1(2) double bond in the A ring and an inert pharmaceutical carrier.

9. A composition of claim 8 wherein the compound contains a double bond only in the 4(5) position.

10. A composition of claim 8 wherein the compound contains a double bond in both the 1(2) and 4(5) positions.

11. A composition of claim 8 wherein the compound is 21-ethyl-$\Delta^4$-pregnene-11$\beta$,17$\beta$-diol-20-yne-3-one.

12. A composition of claim 8 wherein the compound is 21-ethyl-$\Delta^{1,4}$-pregnadiene-11$\beta$,17$\beta$-diol-20-yne-3-one.

13. A composition of claim 8 wherein the compound is 21-isopropenyl-$\Delta^{1,4}$-pregnadiene-11$\beta$,17$\beta$-diol-20-yne-3-one.

14. A composition of claim 8 wherein the compound is 21-methyl-$\Delta^{1,4}$-pregnadiene-11$\beta$,17$\beta$-diol-20-yne-3-one.

15. A composition of claim 8 wherein the compound is 21-methyl-$\Delta^4$-pregnene-11$\beta$,17$\beta$-diol-20-yne-3-one.

16. A method of relieving inflammation in warm-blooded animals comprising administering to warm-blooded animals an anti-inflammatorily effective amount of at least one compound of the formula

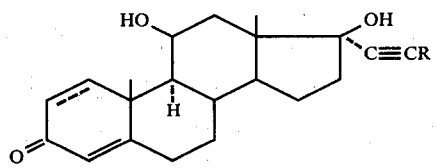

wherein R is saturated and unsaturated alkyl of 1 to 12 carbon atoms and the dotted line indicates the optional presence of a 1(2) double bond in the A ring.

17. A method of claim 16 wherein the compound contains a double bond only in the 4(5) position.

18. A method of claim 16 wherein the compound contains a double bond in both the 1(2) and 4(5) positions.

19. A method of claim 16 wherein the compound is 21-ethyl-$\Delta^4$-pregene-11$\beta$,17$\beta$-diol-20-yne-3-one.

20. A method of claim 16 wherein the compound is 21-ethyl-$\Delta^{1,4}$-pregnadiene-11$\beta$,17$\beta$-diol-20-yne-3-one.

21. A method of claim 16 wherein the compound is 21-isopropenyl-$\Delta^{1,4}$-pregnadiene-11$\beta$,17$\beta$-diol-20-yne-3-one.

22. A method of claim 16 wherein the compound is 21-methyl-$\Delta^{1,4}$-pregnadiene-11$\beta$,17$\beta$-diol-20-yne-3-one.

23. A method of claim 16 wherein the compound is 21-methyl-$\Delta^4$-pregnene-11$\beta$,17$\beta$-diol-20-yne-3-one.

* * * * *